United States Patent [19]

Busey

[11] Patent Number: Plant 7,699

[45] Date of Patent: Oct. 29, 1991

[54] ST. AUGUSTINEGRASS NAMED 'FX-33'

[75] Inventor: Philip Busey, Plantation, Fla.

[73] Assignee: University of Florida, Gainesville, Fla.

[21] Appl. No.: 378,339

[22] Filed: Jul. 7, 1989

[51] Int. Cl.[5] ..... A01H 5/00

[52] U.S. Cl. ..... Plt./88

[58] Field of Search ..... Plt./88

*Primary Examiner*—Howard J. Locker

*Attorney, Agent, or Firm*—J. R. Wetherell, Jr.

[57] ABSTRACT

A perennial, vegetatively propagated St. Augustinegrass genotype having resistance to two populations of the southern chinch bug, resistance to seasonal drought, and many hairs on the young leaf blades.

2 Drawing Sheets

SUMMARY OF THE VARIETY

This invention relates to a new and distinct perennial St. Augustinegrass genotype selected from among double-cross hybrids of parents introduced from Africa. The pedigree was (PI-300127×PI-300130)×(PI-293666×PI-290888) and the four parents were intercrossed by means of emasculation and controlled pollination. The selected hybrid genotype, FX-33, was propagated vegetatively to provide planting stock for studying performance and comparison to presently available commercial varieties.

Genotype FX-33 has resistance to two populations of the southern chinch bug, including a population to which Floratam is susceptible. FX-33 has resistance to seasonal drought and can be used for non-irrigated turf in a humid area such as southern Florida, where shallow subsurface soil moisture occurs. The adaptive advantages of FX-33 and the presence of many hairs on the young leaf blades allow FX-33 to be distinguished from other St. Augustinegrasses.

BRIEF DESCRIPTION OF THE ILLUSTRATIONS

DETAILED DESCRIPTION OF THE VARIETY

The following is a detailed description of the new grass variety, based upon observation of the plant grown under conventional greenhouse conditions, and in outdoor trays on raised benches and in field plots, with color notations based on *Munsell Book of Color: Glossy Finish Edition,* Munsell Color, Baltimore, Md., 1976; and *Munsell Color Charts for Plant Tissues,* Munsell Color, Baltimore, Md., 1977. Color descriptions were supplemented with names approximating the Munsell notations, the names described in Smith, *Naturalist's Color Guide,* The American Museum of Natural History, New York, N.Y., 1975.

The applicant has asexually propagated the invention FX-33 at several other locations in Florida by means of stolon cuttings. Specifically, stolons were cut into segments containing at least one node, planted in soil, and cared for until they rooted and new plants produced. The applicant has discovered the novelty and distinctness of FX-33, compared with all other varieties of St. Augustinegrass.

FX-33 is a perennial, vegetatively propagated genotype of St. Augustinegrass (*Stenotaphrum secundatum*

[Walt.] Kuntze). It grows by creeping or ascendant, dorsiventrally compressed stolons which root at the nodes. Vegetative characters of FX-33 are similar to Floratam and Bitterblue in most respects (Table 1), and cannot be relied on for positive identification of samples, in most cases. Stolon color of FX-33 is 5GY 6/6 (approximately parrot green) with 5RP 3/10 (approximately true purple) chromatic cells are concentrated on the distal end of each internode. In mixture, the green and purple make the distal ends of internodes thus appear to the eye anywhere from 5RP 3/10 (approximately true purple) to 2.5R 3/2 (approximately Hay's Maroon). Blades are plicate, 30 to 360 mm long, and 8 to 11 mm wide, abruptly contracted at the base, obtuse at the apex. Leaf dimensions of St. Augustinegrass genotypes vary greatly in response to age, light level, and other environmental factors. The ligule of FX-33 is a line of hairs. Leaf sheaths are laterally compressed.

Figure 1:
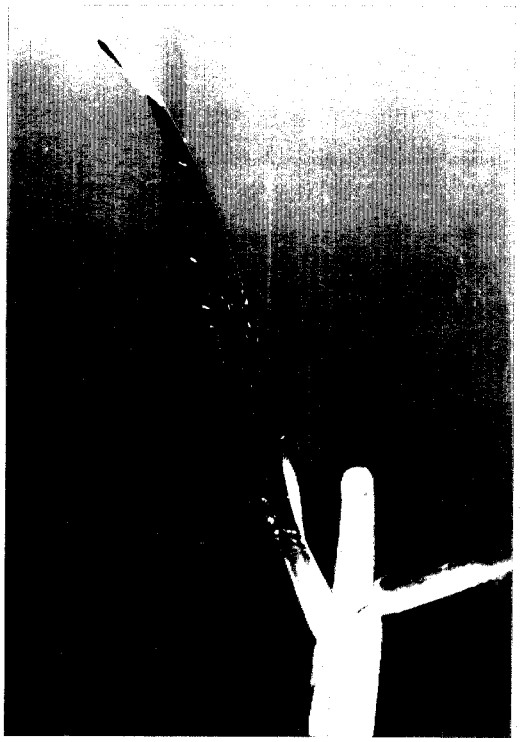
FIG. 1 shows the leaf blade abaxial surface of FX-33.

In contrast with all other cultivated varieties of St. Augustinegrass, FX-33 has abundant hairs on both surfaces of the young leaf blades. The leaf hairs are most abundant on the abaxial surface (Table 2 and FIG. 1), and range from 50 to 350 per abaxial leaf blade surface. Hairs are about 1 mm long and they are discernible to the unaided eye. Other recognized varieties of St. Augustinegrass have no hairs on the leaf blade surfaces, although hairs are present in all varieties on the ligule and collar region. Adaxial leaf color of FX-33 is 5GY 5/6 (approximately parrot green) under typical soil fertility but may vary to 7.5GY 5/4 (approximately grass green) when well fertilized.

Inflorescences of FX-33 are terminal and axillary, subtended by a flag leaf with reduced blade 20 to 40 mm long. The terminal inflorescences are dorsiventrally compressed spike-like panicles, with a floral region 90 to 140 mm long bearing 17 to 20 racemes embedded in pockets on one face of a corky main axis.

Mean floral region length of FX-33, 115.6 mm, is shorter than that of Floratam, but longer than that of Bitterblue. The non-flowering peduncle-like region below the floral region is extremely variable, 40 to 120 mm long. The axillary inflorescences are variable and much reduced in size compared with the terminal inflorescences. On terminal inflorescences, each raceme has 1 or 2 (occasionally 3) spikelets on an inconspicuous rachis.

Spikelet length in St. Augustinegrass was shown to be adequately free of environmental effects for use in variety description and identification (Busey, *Crop Sci.,*

Figure 2:
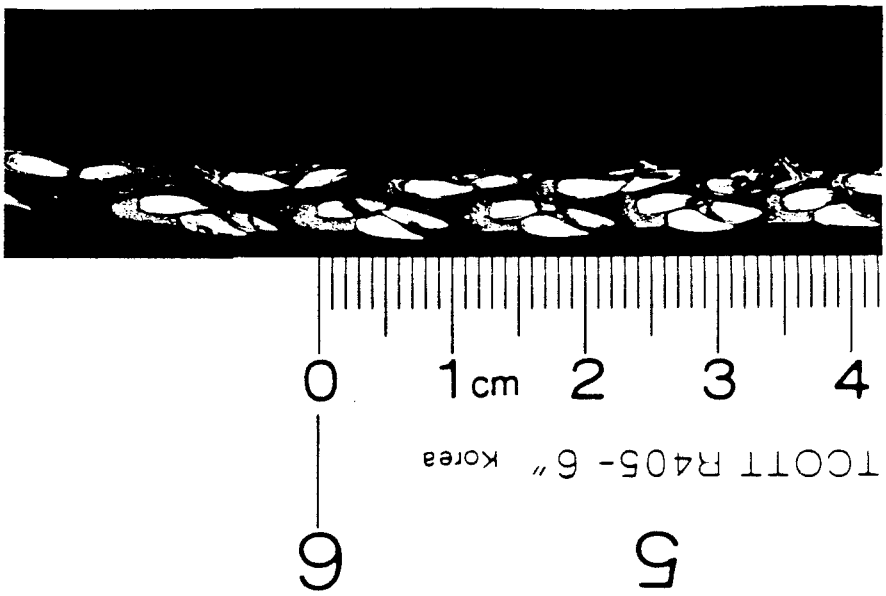
FIG. 2 shows the inflorescence mid-section of FX-33.

26:28, 1986). Spikelets of FX-33 are narrowly ovate, slightly acuminate, 4.8 to 5.2 mm long, and about 1.7 mm wide, and awnless. Spikelets of FX-33 (FIG. 2) are about the same length as those of Bitterblue (TABLE 3), but are shorter than those of Floratam (and Floralawn), which >5.2 mm (Busey, *ibid,* 1986). Spikelets of FX-33 are much longer than those of Breviflorus Race varieties (e.g., Seville), which are <4.5 mm. Glumes are membranaceous, the lower (and outer) glume truncate and about 1 mm long, nerveless, the upper (and inner) glume about the full size of the spikelet and lemmas. The lower (and outer) floret is staminate, the upper (and inner) bisexual, its lemma with 5 or 6 longitudinal nerves and about equal in size to the spikelet. Genotype FX-33 has anther color 10YR 7/12 (approximately deep chrome), stigma color 5RP 3/10 (approximately true purple), and an unreduced chromosome number of 30 (TABLE 4). Chromosomes of FX-33 associate in diakinesis principally as bivalents with regular disjunction (Busey, *Crop Sci.,* 30:588, 1990), while pairing and disjunction in Floratam are irregular (Busey, *Proc.Fla.-Hort.Sci.Soc.,* 92:228, 1979). The chromosome number of Floratam (2n=32) is based on an average of tapetal cells, which are more stable than microsporocytes (Busey, *Proc.Fla.Hort.Sci.Soc.,* 92:228, 1979), but are still subject to an observed range from 30 to 34, which is not explained. Iodine pollen stainability of FX-33 is high (89%) compared with Floratam (32%), Bitterblue (32%) and Floratine (0%). FX-33 has moderate (33%) seed fertility. FX-33 differs from its female parent 300127-8 (=300127×300130) by field performance characteristics. In the field, FX-33 displays less incidence of leaf spot disease, and higher visual quality ratings, than the female parent 300127-8. In contrast to the male parent 293666-11 (=293666×290888), however, which has occasional leaf blade hairs, FX-33 has very abundant leaf blade hairs.

In southern Florida, FX-33 survives seasonal drought with no irrigation, with slight reduction in canopy coverage after 15 months (Table 6). Under the same experimental conditions, the most widely grown variety of this region, Floratam St. Augustinegrass, shows severe loss of canopy coverage due to drought. The southern Florida region is subject to seasonal drought, due to seasonally variable rainfall and sand soils which have little water holding capacity. Nevertheless, this is a humid region and under experimental conditions where FX-33 has shown drought survival, there is a relatively shallow (1.4 m) aquifer and relatively shallow (0.6 m) zone of moist soil associated with a jagged rock substrate. Although the majority of FX-33 root mass is in the upper 0.6 m, some FX-33 roots have been observed in the aquifer. It is thus possible that the deep roots of FX-33 remove moisture from the continuously moist soil zone.

During drought, the duration permanent wilt of FX-33 is brief and is significantly less than Floratam, thus FX-33 is most likely drought resistant by means of avoidance, rather than tolerance. It is not known whether the drought resistance of FX-33 will be adequate for its survival without irrigation when it is grown in coastal ridges, central highlands, or sloped areas, which are drier than typical turf-covered areas of southern Florida.

Turfgrass quality ratings of FX-33 are comparable or superior to Floratam and Bitterblue in a pre-stress establishment period under supplemental irrigation (Table 7). In the second growing season, and after withholding irrigation (Post-stress ratings, Table 7), FX-33 shows no reduction in quality ratings, while Floratam is severely damaged and shows reduced quality ratings. FX-33 is usable as a non-irrigated turfgrass in southern Florida. This is an important region for growing turfgrass, and primarily St. Augustinegrass lawns are used by 4 million inhabitants. The usefulness of a non-irrigated variety of St. Augustinegrass could be large.

FX-33 is resistant to the PDP (Polyploid Damaging Population, Busey and Center, *J. Econ. Ent.,* 80:60, 1987) southern chinch bug which has damaged Floratam in Florida since 1985 (Table 8). In the same laboratory tests, Floratam was susceptible to the PDP southern chinch bug, based on high oviposition rate and extended survival of PDP bugs on Floratam. FX-33 is also resistant to the STD (Busey and Center, *ibid,* 1987) population of southern chinch bug, based on reduced oviposition rate and no survival of adult bugs after 35 days confinement on FX-33. This compares with excellent survival and oviposition rate of bugs on susceptible genotypes (Table 9). In this respect FX-33 is similar to Floratam, which has been recognized to be resistant to the southern chinch bug. The resistance of FX-33 to both bug populations is important, because the southern chinch bug is the most important insect pest of St. Augustinegrass in Florida, and has damaged Floratam in 37 counties of Florida.

FX-33 often displays noticeable leaf spotting, which is tentatively identified as gray leaf spot disease (TABLES 5 and 10). The variability in symptoms can be summarized as follows: When other genotypes such as Bitterblue and Floratam are only moderately affected, FX-33 shows less incidence of symptoms than those cultivars (e.g., November, 1987; and July, 1989, TABLE 10); when other genotypes are severely affected (e.g., August, 1984, TABLE 5); and July, 1989, TABLE 10), FX-33 shows greater comparative incidence of symptoms. The leaf spots on FX-33 are small (c. 1 mm in diameter), very numerous black, and do not generally develop a tan center. The disease occurs on mature growth as well as young stolons, is severe in sandy soil, and not conspicuous in organic soil. It is not known whether the cause of variable symptom expression is due to different disease organisms in different environments and evaluations, or due to genotype X environmental interactions in host expression.

FX-33 covers the soil at approximately the same rate as Floratam (TABLE 6 and TABLE 11); however, this is due to higher density, and despite lower rate of lateral stolon extension, of FX-33 compared with Floratam. This is explained by the fact that the stolons of Floratam are poorly branched near the stolon tips, while those of FX-33 are highly branched. FX-33 is highly susceptible to atrazine applied in sand soil (TABLE 11).

TABLE 1

Vegetative characteristics of FX-33 and other St. Augustinegrasses[1]

| Selection/ Variety | Internode Length (mm) | Internode Thickness (mm) | Leaf blade Length (mm) | Leaf blade Width (mm) |
|---|---|---|---|---|
| FX-33 | 20.9 ± 0.3 | 3.0 ± 0.1 | 33.0 ± 4.5 | 8.8 ± 0.3 |
| Floratam | 23.1 ± 1.3 | 3.4 ± 0.1 | 36.8 ± 4.1 | 8.6 ± 0.3 |
| Bitterblue | 20.4 ± 0.8 | 3.1 ± 0.1 | 34.4 ± 3.1 | 8.7 ± 0.3 |

[1]Field planting, Fort Lauderdale, Florida, Planted: August, 1987. Data: October 1988. Plants were drought conditioned at the time of data collection.

TABLE 2

Pubescence on leaves of FX-33 and other St. Augustinegrasses[1]

| Selection/Variety | Adaxial Surface (hairs/leaf) | Abaxial surface (hairs/leaf) |
|---|---|---|
| FX-33 | 51 ± 23 | 219 ± 42 |
| Bitterblue | 0 | 0 |
| Delmar (Scotts 6-72-99) | 0 | 0 |
| Floralawn (FA-108) | 0 | 0 |
| Floratam (FA-110) | 0 | 0 |
| Floratine (FA-20) | 0 | 0 |
| Florida Common | 0 | 0 |
| Jade (Scotts 6-72-182) | 0 | 0 |
| Raleigh (NCSA-21) | 0 | 0 |
| Seville (Scotts 6-68-516) | 0 | 0 |
| Sunclipse (Scotts 6-72-130) | 0 | 0 |

[1]Based on five or more leaves of each selection/variety. Values following the ± symbol are standard errors of the means.

TABLE 3

Inflorescence characteristics of FX-33 and other St. Augustinegrasses[1]

| Selection/ variety | Spikelet length (mm) | Glume length (mm) | Floral region length (mm) |
|---|---|---|---|
| FX-33 | 5.09 ± 0.09 | 0.98 ± 0.03 | 115.6 ± 6.0 |
| Bitterblue | 4.96 ± 0.06 | 1.11 ± 0.07 | 84.0 ± 2.2 |
| Floralawn | 5.76 ± 0.08 | 1.59 ± 0.06 | 105.6 ± 4.6 |
| Floratam | 5.74 ± 0.10 | 1.75 ± 0.07 | 129.2 ± 5.0 |
| Raleigh | 4.23 ± 0.07 | 1.55 ± 0.05 | 63.0 ± 1.7 |
| Seville | 4.22 ± 0.07 | 1.10 ± 0.09 | 73.0 ± 1.7 |

[1]Nursery trays, Fort Lauderdale, Florida, Data: July, 1989. Values following the ± symbol are standard errors of the means.

TABLE 4

Another color, stigma color, and chromosome number of FX-33 and other St. Augustinegrasses.

| Selection/ Variety | Anther color | Stigma color | Chromosome number |
|---|---|---|---|
| FX-33 | Orange Yellow | Purple | 30 |
| Delmar | — | White | 18 |
| Floralawn | Orange Yellow | Purple | — |
| Floratam | Orange Yellow | Purple | 32 |
| Bitterblue | Orange Yellow | Purple | — |
| Floratine | Orange Yellow | Purple | 27 |
| Florida Common | — | — | 18 |
| Jade | — | — | 18 |
| Roselawn | Orange Yellow | Purple | 18 |
| Raleigh | Sulfur Yellow | White | 18 |
| Seville | Sulfur Yellow | Bicolor[1] | 18 |

[1]White stigma branches and purple stigma shaft.

TABLE 5

Leaf spot rating, visual leaf hairiness rating, and visual quality ratings of FX-33, its antecedents, and named cultivars

| Selection/ variety | Relation | Leaf spot[1] rating | Hair-iness[2] | Visual quality rating[3] Year 1[4] | Year 2[5] |
|---|---|---|---|---|---|
| Bitterblue | Cultivar | 8.1 ± 0.4 | 1.0 ± 0.0 | 3.1 ± 0.3 | 3.8 ± 0.5 |
| Floratam | Cultivar | 7.0 ± 0.4 | 1.0 ± 0.0 | 5.3 ± 0.4 | 5.6 ± 0.9 |
| 300127-8 | Female parent | 9.3 ± 0.3 | 4.0 ± 0.0 | 4.1 ± 0.9 | 4.5 ± 1.0 |
| 293666-11 | Male parent | 8.3 ± 0.3 | 3.5 ± 0.5 | 6.1 ± 1.1 | 5.8 ± 0.3 |
| FX-33 | Progeny | 8.3 ± 0.8 | 4.5 ' 0.9 | | |
| 300127-8 | Female parent | 9.3 ± 0.3 | 4.0 ± 0.0 | 4.1 ± 0.9 | 4.5 ± 1.0 |
| 293666-11 | Male parent | 8.3 ± 0.3 | 3.5 ± 0.5 | 6.1 ± 1.1 | 5.8 ± 0.3 |

TABLE 5-continued

Leaf spot rating, visual leaf hairiness rating, and visual quality ratings of FX-33, its antecedents, and named cultivars

| Selection/ variety | Relation | Leaf spot[1] rating | Hair-iness[2] | Visual quality rating[3] Year 1[4] | Year 2[5] |
|---|---|---|---|---|---|
| FX-33 | Progeny | 8.3 ± 0.8 | 4.5 ± 0.5 | 4.9 ± 0.4 | 5.8 ± 2.3 |

[1]Rating 1 = no spots; 10 = severe spots. Values following the ± symbol are standard errors of the means. Field data Fort Lauderdale, Florida, August 1984; field area planted June 1984.
[2]Rating 1 = no hairs; 5 = very hairy; evaluated December 1984; same field areas as above.
[3]Rating 10 = best possible, 1 = dead; same field area as above.
[4]Mean of ratings taken August and December 1984 and February and May 1985.
[5]Mean if ratings taken September 1985 and March 1986.

TABLE 6

Pre-stress and post-stress canopy coverage, and duration permanent wilt of FX-33 and other St. Augustinegrasses associated with withholding irrigation during a seasonal drought[1]

| Selection/ Variety | Canopy Coverage pre-stress (%) | 2 mos. post-stress (%) | 15 mos. post-stress (%) | Duration permanent wilt (days) |
|---|---|---|---|---|
| FX-33 | 99 ± 1 | 99 ± 1 | 94 ± 3 | 0.8 ± 0.5 |
| Floratam | 97 ± 2 | 36 ± 9 | 43 ± 11 | 21.5 ± 1.6 |
| Bitterblue | 99 ± 1 | 97 ± 2 | 93 ± 5 | 6.3 ± 2.9 |

[1]Field planting, Fort Lauderdale, Florida. Planted: August 1987. Data: March 1988 through June, 1989. During March and the first part of April (41 dyas) only 32 mm rain was received, which was followed by a period of adequate rainfall. Values following the ± symbol are standard errors of the means.

TABLE 7

Turfgrass quality ratings of FX-33 and other St. Augustinegrasses[1]

| Selection/Variety | Pre-stress[2] | Post-stress[3] |
|---|---|---|
| FX-33 | 7.7 ± 0.1[4] | 7.6 ± 0.1 |
| Floratam | 6.0 ± 0.3 | 3.9 ± 0.5 |
| Bitterblue | 7.5 ± 0.3 | 7.5 ± 0.3 |

[1]Field planting, Fort Lauderdal, Florida. Planted: August 1987.
[2]Data: December, 1987 and February, 1988, mean of two dates of evaluation.
[3]Data: June, 1988 through June, 1989, mean of 13 monthly evaluations.
[4]Turfgrass quality rated on a 1 to 10 scale, with 10 = best, 1 = worst, and 7 = acceptable. Values following the ± symbol are standard errors of the means.

TABLE 8

Longevity, oviposition rate, and reproduction of adult PDP southern chinch bugs confined on FX-33 and other St. Augustinegrasses[1]

| Sdult PDP southern chinch bugs confined on FX-33 and other St. Augustine-grasses[1] | source | Lon- | oviposition rate (eggs/ | Repro-duction (eggs/ | Host |
|---|---|---|---|---|---|
| Selection/ Variety | source of Bugs | Lon-gevity (days) | oviposition rate (eggs/ female/ week) | Repro-duction (eggs/ female/ lifetime | Host Suit-ability |
| | | Experiment #1 | | | |
| Floratam | Lab | 45.4 ± 6.1 | 11.5 ± 1.0 | 65 ± 17 | Suscep-tible |
| FX-33 | Lab | 21.2 ± 4.1 | 2.7 ± 0.5 | 7 ± 2 | Resistant |
| | | Experiment #2 | | | |
| Floratam | Field | 97.0 ± | 15.6 ± 0.6 | 199 ± 16 | Suscep- |

TABLE 8-continued

Longevity, oviposition rate, and reproduction of adult PDP southern chinch bugs confined on FX-33 and other St. Augustinegrasses[1]

| Sdult PDP southern chinch bugs confined on FX-33 and other St. Augustine-grasses[1] | source | Lon- | oviposition rate (eggs/ | Repro-duction (eggs/ | Host |
|---|---|---|---|---|---|
| Selection/ Variety | source of Bugs | Lon-gevity (days) | oviposition rate (eggs/ female/ week) | Repro-duction (eggs/ female/ lifetime | Host Suit-ability |
| | | 7.6 | | | tible |
| FX-33 | Field | 32.7 ± 4.7 | 4.5 ± 1.0 | 19 ± 7 | Resistant |
| | | Experiment #3: | | | |
| Floratam | Lab | 61.3 ± 7.6 | — | — | Suscep-tible |
| Bitterblue | Lab | 56.4 ± 5.7 | — | — | Suscep-tible |
| FX-33 | Lab | 11.4 ± 1.4 | — | — | Resistant |
| | | Experiment #4 | | | |
| Floratam | Field | 86.3 ± 14.5 | 18.8 ± 1.1 | 209 ± 52 | Suscep-tible |
| FX-33 | Field | 21.6 ± 5.0 | 3.0 ± 1.0 | 7 ± 3 | Resistant |
| | | Experiment #5 | | | |
| Floratam | Field | 58.8 ± 13.1 | 18.2 ± 1.4 | 149 ± 34 | Suscep-tible |
| FX-33 | Field | 16.5 ± 4.7 | 5.2 ± 1.2 | 15 ± 3 | Resistant |
| | | Weighted mean | | | |
| Floratam | — | 72.7 | 16.0 | 125 | Suscep-tible |
| Bitterblue | — | 56.4 | — | — | Suscep-tible |
| FX-33 | — | 21.8 | 3.9 | 14 | Resistant |

[1]Each experiment involved between 16 and 76 chinch bugs and between 8 and 18 female chinch bugs on each grass selection/variety. Values following the ± symbol are standard errors of the means. All bugs were maintained by replacing grass food source weekly for the natural lifetime of the bugs.

TABLE 9

Survival and oviposition rate of adult STD southern chinch bugs confined on FX-33 and other St. Augustinegrasses

| Selection/ Variety | Survival after 35 days[1] (%) | Oviposition rate[2] (eggs/ female/week) | Host suitability |
|---|---|---|---|
| FX-33 | 0 | 1.0 ± 0.3 | Resistant |
| Floratam | 5 | 1.2 ± 0.3 | Resistant |
| Bitterblue | 70 | 11.7 ± 2.1 | Susceptible |
| Seville | 73 | 16.5 ± 2.2 | Susceptible |
| Florida Common | 78 | 22.4 ± 2.8 | Susceptible |

[1]Based on 20 male and 20 female chinch bugs for each selection/variety.
[2]Based on 20 female chinch bugs for each selection/variety. Values following the ± symbol are standard errors of the means.

TABLE 10

Leaf spot rating of FX-33 and other St. Augustinegrasses[1]

| | November, 1987[2] | July, 1989[2] | July, 1988[3] |
|---|---|---|---|
| FX-33 | 2.3 ± 0.3 | 6.9 ± 0.4 | 3.9 ± 0.4 |
| Floratam | 4.5 ± 0.6 | 6.4 ± 0.2 | 4.8 ± 0.4 |
| Bitterblue | 4.1 ± 0.4 | 6.5 ± 0.6 | 5.7 ± 0.3 |

[1]Rating 1 = no spots; 10 = severe spots. Values following the ± symbol are standard errors of the means.
[2]Field planting, Fort Lauderdale, Florida. Planted: August 1987.
[3]Field planting, LaBelle, Florida. Planted: May 1988.

TABLE 11

Production characteristics of FX-33 and other St. Augustinegrasses

| | Cover (3 mos.)[1] (%) | Lateral Stolon Extension[2] | Density[2] | Atrazine Damage[3] |
|---|---|---|---|---|
| FX-33 | 65.0 ± 9.1 | 7.1 ± 0.3 | 7.5 ± 0.3 | 91.3 ± 3.7 |
| Floratam | 66.3 ± 9.3 | 9.5 ± 0.2 | 3.3 ± 0.2 | 12.5 ± 5.7 |
| Bitterblue | 66.9 ± 6.3 | 8.0 ± 0.2 | 5.2 ± 0.2 | 41.7 ± 9.7 |

[1]Field planting, Fort Lauderdale. Planted: August 1987. Data: November 1987.
[2]Field planting, LaBelle, Florida. Planted: May 1988. Data: July 1988. Stolon extension and density rated on a 1 to 10 scale, with 10 = greatest, 1 = least. Spread
[3]Percent of lost canopy. Field planting, LaBelle, Florida. Planted: May 1988. Data: May 1989.

I claim:

1. A new and distinct variety of St. Augustinegrass, substantially as herein illustrated and described, characterized by its many hairs on the young leaf blades, its superior resistance to seasonal drought when grown in a humid region with shallow subsurface soil moisture, and its resistance to STD and PDP populations of the southern chinch bug.

* * * * *